US012709599B2

(12) United States Patent
Bertolla et al.

(10) Patent No.: US 12,709,599 B2
(45) Date of Patent: Aug. 18, 2026

(54) PROCESS FOR PRODUCING EPSILON-CAPROLACTAM BY DEPOLYMERIZATION OF POLYCAPROLACTAM (PA6)

(71) Applicant: AQUAFIL S.P.A., Arco (IT)

(72) Inventors: Maddalena Bertolla, Mori (IT); Michele Cecchetto, Ledro (IT); Anacleto Dal Moro, Semonzo di Borso del Grappa (IT); Michele Modesti, Padua (IT); Stefano Guerra, San Giovanni Lupatoto (IT)

(73) Assignee: AQUAFIL S.P.A., Arco (IT)

( * ) Notice: Subject to any disclaimer, the term of this patent is extended or adjusted under 35 U.S.C. 154(b) by 347 days.

(21) Appl. No.: 18/688,863

(22) PCT Filed: Nov. 10, 2022

(86) PCT No.: PCT/IB2022/060831

§ 371 (c)(1),
(2) Date: Mar. 4, 2024

(87) PCT Pub. No.: WO2023/084441

PCT Pub. Date: May 19, 2023

(65) Prior Publication Data

US 2024/0383859 A1 Nov. 21, 2024

(30) Foreign Application Priority Data

Nov. 10, 2021 (IT) ........................ 102021000028601

(51) Int. Cl.
*C07D 223/10* (2006.01)

(52) U.S. Cl.
CPC .................................. *C07D 223/10* (2013.01)

(58) Field of Classification Search
None
See application file for complete search history.

(56) References Cited

U.S. PATENT DOCUMENTS 5,294,707 A 3/1994 Kotek
5,430,068 A 7/1995 Subramanian
5,668,277 A 9/1997 Hendrix et al.
5,977,193 A 11/1999 Corbin et al.
6,087,494 A 7/2000 Thomissen
6,342,555 B2 1/2002 Sifniades et al.
2019/0382339 A1 12/2019 Dal Moro et al.
2020/0148835 A1 5/2020 Paleologou et al.

FOREIGN PATENT DOCUMENTS

EP 0522235 A1 1/1993
KR 940006530 B1 7/1993
WO WO-2004031146 A1 4/2004

OTHER PUBLICATIONS

Office Action issued Dec. 26, 2025, in corresponding Korean Patent Application No. 202447036106, 7 pages.
International Search Report and Written Opinion issued Jan. 20, 2023 in PCT/IB2022/060831, 11 pages.
C.D. Papaspyrides et al, "Recycling of glass fiber reinforced thermoplastic composites. I. Ionomer and low density polyethylene based composites", Resources, Conservation and Recycling 14, 1995, pp. 91-101.
Dr. F. Kreklau, "Carpet Recycling for Europe: The "Polyamide 2000" Project", MG Engineering, Session IV, 2000, pp. 1-7 plus cover page.

*Primary Examiner* — Sarah Pihonak
*Assistant Examiner* — Donna M Nestor
(74) *Attorney, Agent, or Firm* — Element IP, PLC

(57) ABSTRACT

The present invention relates to a process for producing ε-caprolactam by depolymerization of polycaprolactam (PA6) which comprises: a. contacting a composite material comprising PA6 and at least one fibrous reinforcing material with a solvent comprising at least one polyol, at a temperature in the range 130° C. 200° C. so as to obtain a solution comprising solubilized PA6 and an insoluble fraction comprising at least said fibrous reinforcing material; b. separating said insoluble fraction from said solution; c. combining said solution with a coagulation liquid comprising water to obtain a partially depolymerized coagulated PA6 dispersed in a liquid phase; d. separating said coagulated PA6 from said liquid phase; e. subjecting said coagulated PA6 separated in said phase d to further depolymerization by hydrolysis to obtain ε-caprolactam.

17 Claims, 1 Drawing Sheet

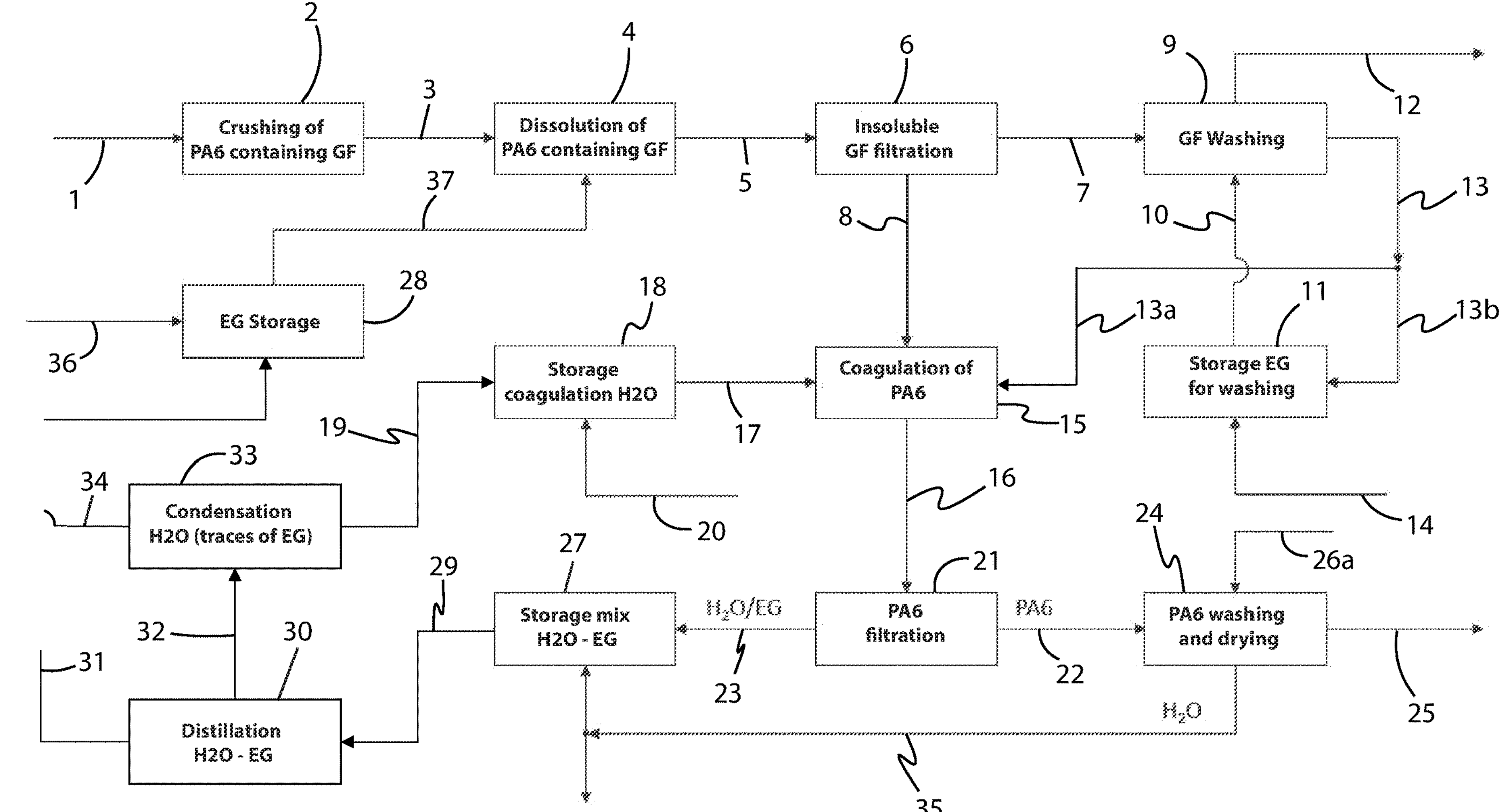
Crushing of PA6 containing GF
Dissolution of PA6 containing GF
Insoluble GF filtration
GF Washing
EG Storage
Storage coagulation H2O
Coagulation of PA6
Storage EG for washing
Condensation H2O (traces of EG)
Storage mix H2O - EG
PA6 filtration
PA6 washing and drying
Distillation H2O - EG
$H_2O$/EG
PA6
$H_2O$
1
2
3
4
5
6
7
8
9
10
11
12
13
13a
13b
14
15
16
17
18
19
20
21
22
23
24
25
26a
27
28
29
30
31
32
33
34
35
36
37

PROCESS FOR PRODUCING EPSILON-CAPROLACTAM BY DEPOLYMERIZATION OF POLYCAPROLACTAM (PA6)

The present invention concerns a process for producing ε-caprolactam by depolymerization of polycaprolactam (PA6). In particular, the present invention concerns the depolymerization of the polycaprolactam contained in a composite material comprising at least one fibrous reinforcing material.

As is well known, polycaprolactam or polyamide-6 (PA6) is a semi-crystalline thermoplastic polymer with excellent thermal, mechanical and chemical resistance properties, which allow it to be used in various application sectors, such as textiles, automotive, electrical and electronic components, construction, coatings, etc. In particular, PA6 is widely used in the Engineering Plastic sector to produce composite products, i.e. materials in which the aforementioned polymer is used in combination with one or more additional fibrous reinforcing materials, such as glass fibres, carbon fibres, polymeric fibres and the like, which increase the mechanical properties thereof.

Recycling of composite materials containing PA6 is currently mainly carried out by mechanical means. That is, composite materials of both post-industrial and post-consumer origin are treated by processes of shredding, grinding, screening, washing, densification, etc., in order to obtain a material in a size suitable for use in new production cycles as a partial replacement of the virgin polymer.

Mechanical recycling, however, has the disadvantage that it only allows the production of new products of lower quality (downgrading) than the products that generated the waste, as the mechanical properties of the polymeric material degrade with use. Furthermore, the presence of colouring compounds prevents the polymer from being reused in all its potential applications. A further problem is the accumulation of additives and contaminants in the polymer material as the reuse cycles of the end-of-life-polymer are repeated.

In reinforced composite materials, fibres are selected according to specific dimensional and mechanical characteristics to achieve the desired improvement. The case of PA6 without and with glass fibre fillers is cited as an example, where different mechanical properties can be improved by means of these fibres, as illustrated in the following table:

Properties of PA6 as is and Reinforced with Glass Fibre

| | | PA6 as is | PA6 glass-fibre reinforced |
|---|---|---|---|
| Fibre glass | % | 0 | 30 |
| Density | g/cm$^3$ | ~1.1 | ~1.4 |
| Elastic modulus | MPa | ~3000 | ~9000 |
| Breaking load | MPa | ~80 | ~180 |

However, the improvement in mechanical properties that can be achieved through the manufacture of composite materials, in particular with glass fibre or other inorganic fibres, is accompanied by difficult recycling of these materials. In fact, the methods for the end-of-life recycling of these products are essentially relegated to mechanical recycling, which imposes major limits on the reuse of the recovered polymer, as the mechanical properties of the polymer deteriorate with the use of the products: this generally forces the recycled polymer to be used almost exclusively in a mixture with virgin polymer.

On the other hand, there is an increasing need for the recycling of materials, especially plastics, in order not to release contaminating and non-biodegradable substances into the environment and to meet the targets of reducing $CO_2$ emissions from fossil fuels. In addition, recycling is often made compulsory by regulations in force, which prohibit the disposal of certain materials in landfill and require that new products be manufactured using increasingly higher quantities of recycled materials.

Physical-mechanical recycling, while widely used, is still a route that leads to the downgrading of the material, whereas the preferred route is that which leads to their upgrading. Upgrading by chemical means leads to obtaining the starting raw material again (in the case of polymers, the starting monomers) with which it is then possible to produce new products of the same quality as those obtainable from virgin materials of oil origin, using the same methods as those used to produce the latter.

A chemical recycling method, described in numerous studies and patents, is based on the dissolution of the polymer and the composites containing it by means of a solvent, followed by the separation by filtration of the insoluble materials, the removal of the remaining impurities (e.g. pigments and other additives added to the polymer during the production process) and the subsequent recovery of the polymer by evaporation of the solvent or by other techniques that return the polymer to a solid phase, generally in the form of granules.

Examples can be cited:

- the process described in the publication Papaspyrides, C. D., J. G. Poulakis, and C. D. Arvanitopoulos, "Recycling of glass fiber reinforced thermo-plastic composites. I. Ionomer and low density polyethylene based composites.", Resources, conservation and recycling 14.2 (1995): 91-101), which involves dissolving glass-fibre filled LDPE in toluene and then separating the polymer from the fibre;
- the PVC regeneration process by impurity separation proposed by VinyLoop, which involves the selective dissolution of PVC in solvent.

To date, the technique of separating the polymer from the fibres and other impurities by dissolving the polymer that forms the composite material has not yielded optimal results, as part of the additives remain in the polymer anyway, altering its appearance also in terms of colour, thus always imposing severe limitations on the possibilities of using the recycled polymer. In particular, particles of various chemical compositions, especially inorganic solids, remain in the polymer, rendering the recovered polymer unusable in important production sectors, such as spinning processes in the textile industry, where polyamides and polyesters of synthetic origin are mainly used.

The above-mentioned disadvantages of mechanical recycling and recycling via solvent dissolution of polymers, together with the increasingly perceived need to protect the environment by applying the principles of the circular economy, make it highly desirable to be able to chemically recycle composite materials containing PA6 to produce the starting monomer ε-caprolactam again, as is already the case, for example, for materials in which PA6 is contained in a mixture with relatively small quantities of foreign materials (e.g. Nylon 6 yarn or textile substrates, or fractions from the separation of polyamide from carpets, tiles, various types of Engineering Plastic, etc.).

In chemical recycling, the scrap or waste containing PA6 undergoes a treatment process through which the polymer chains are depolymerized to obtain the original monomer (ε-caprolactam) which, once purified, possesses the same quality as the virgin monomer and can therefore be used without any particular limitations to produce new, high quality products.

The depolymerization of PA6 has been a known chemical process for many years, which has also been applied industrially, for example in processes known as Evergreen (Depolymerization of polyamides, U.S. Pat. No. 5,668,277, 1997) and Polyamide 2000 (POLYAMIDE 2000-WORLD CONGRESS: The Polyamide Chain Resins, Products, Developments, Technologies, Markets, March 14-15-16, 2000, Zurich, Switzerland).

In the state of the art, several processes have been proposed to depolymerize PA6, such as thermal hydrolysis, ammonolysis, solvolysis and thermal decomposition processes under pyrolysis conditions in supercritical fluids. Among these processes, depolymerization by thermal hydrolysis, in the presence or absence of a catalyst, is one of the most promising chemical recycling alternatives due to its possible application and implementation on an industrial scale.

In general, hydrolytic depolymerization involves the treatment of PA6 in its molten state with water in the form of steam, at a temperature in the range 200° C.-450° C. and pressure 0.2-20.0 bar, with the formation of the monomer ε-caprolactam. The monomer is separated in the vapour phase from the depolymerization mixture (e.g. by stripping with a stream of water vapour), condensed and then purified to remove impurities and unwanted reaction by-products.

Examples of hydrolytic depolymerization processes are described for example in U.S. Pat. Nos. 6,087,494 and 5,294,707.

Known depolymerization processes, whether of the hydrolytic or other type, have the practical disadvantage that they cannot directly process PA6-based composites that contain fibrous reinforcing materials in high quantities. In fact, inorganic fibrous material tends to accumulate in the depolymerization reactor, creating solid residues and fouling that are very difficult to remove, requiring the depolymerization plant to constantly stop running.

A second problem that industrially affects PA6 depolymerization processes is the duration of the depolymerization reaction, which depends, among other factors, on the molecular weight of the PA6 chains undergoing depolymerization. Although numerous catalysts have been studied in the art to accelerate the depolymerization reaction and/or to make it take place more quickly, the need to reduce the duration of the depolymerization step remains, as this would increase the productivity of the ε-caprolactam production process.

A process for recovering polyamide, particularly PA66 and PA6, from process waste or post-consumer products containing it in a mixture with foreign materials, such as fibrous reinforcing materials like glass fibres, is described in U.S. Pat. No. 5,430,068. The process described in this patent involves: (1) dissolution of the polyamide in an anhydrous polyol or in an aliphatic carboxylic acid with 2 to 6 carbon atoms at high temperature; (2) separation of extraneous materials from the polyamide solution; (3) combination of the polyamide solution with an additional quantity of the same solvent at a temperature sufficiently lower than that of the polyamide solution so as to rapidly cool the solution and cause the precipitation of the polyamide; (4) recovery of the precipitated polyamide. In one embodiment, the solvent used for the dissolution of PA66 or PA6 is a glycol, such as ethylene glycol (EG) or propylene glycol (PG). The process aims to recover the polyamide in an essentially undegraded form, i.e. causing the smallest possible reduction in its molecular weight (controlled via Relative Viscosity analysis), so that it can be reused in extrusion or moulding processes.

The PA6 recoverable from a composite material by the above-mentioned process, i.e. by dissolution at high temperature and subsequent precipitation of the solid polyamide always and exclusively by contact with the solvent glycol, however, is not per se suitable for undergoing a depolymerization process to obtain ε-caprolactam, particularly by hydrolysis, since the dissolution treatment in EG or PG at high temperature also promotes the reaction of the terminal carboxyl groups of the PA6 chains with the solvent itself and the consequent formation of ester groups with EG or PG. The presence of these esterified groups in PA6 results in the introduction of non-negligible amounts of EG or PG into the depolymerization mixture, which adversely affects the yield of the depolymerization reaction and the quality of the ε-caprolactam obtained. Indeed, in the depolymerization step, EG and PG glycols are released from the esterified end groups, which, under reaction conditions, form light by-products that evaporate together with the caprolactam monomer. By-products include the glycols themselves and their derivatives, such as esters of short-chain organic acids, hydroxy acids, lactones formed by the cyclization of said hydroxy acids, unsaturated ketones and others. These by-products, which can also be present in relatively high proportions, are difficult to separate from caprolactam, either using chemical treatments or by performing various distillation steps, with a significant impact on purification costs and the final quality of the monomer obtained. Where present, these by-products also interfere in the polymerization processes of recycled ε-caprolactam.

In view of the aforementioned state of the art, the Applicant addressed the problem of providing a depolymerization process for PA6 to produce the monomer ε-caprolactam that overcomes the drawbacks of the known art.

In particular, an object of the present invention is to provide a depolymerization process to produce ε-caprolactam that is applicable to a composite material comprising PA6 blended with at least one fibrous reinforcing material also in a significant quantity.

A further aim of the present invention is to provide a process for the production of ε-caprolactam in which the depolymerization stage is performed in a relatively short time and with a high conversion yield of PA6, thus increasing the productivity of the process.

It has now been found that the aforementioned and other purposes, which will be better explained in the following description, can be achieved by subjecting the composite material to a pre-treatment to separate the fibrous material (and possibly other foreign materials), which is conducted under conditions that allow the PA6 to be recovered in a partially depolymerized form and thus more easily and rapidly hydrolytically depolymerized to ε-caprolactam, resulting in an increase in the overall productivity of the process.

The process according to the present invention also makes it possible to use composite materials based on PA6 and reinforcing fibres, e.g. from the Engineering Plastics sector, in PA6 chemical recycling processes.

Separation of the fibrous material is achieved by treating the composite material under heat (130° C.-200° C.) with a solvent comprising at least one polyol, preferably a glycol, so as to obtain an initial suspension comprising solubilized PA6 and an insoluble fraction comprising the fibrous material that is easily separable from the PA6 solution. The PA6 solution is then placed in contact with a water-based coagulation liquid to generate coagulated PA6 in a partially depolymerized form. It was surprisingly found that the coagulation of PA6 solubilized in a polyol by water, instead of by the polyol itself as described in U.S. Pat. No. 5,430,068, inhibits the esterification of the carboxyl end-groups of the polyamide by the polyol, thus favouring the production of ε-caprolactam of higher quality in the subsequent stage of completion of the depolymerization by hydrolysis.

Thanks to the removal of the fibrous material and the recovery of a partially depolymerized PA6 substantially devoid of esterified end groups, the process of the present invention makes it possible to effectively apply hydrolytic depolymerization to chemically recycle the PA6 contained in composite materials, thus making it possible to use these materials, hitherto disposed of in landfill or mechanically recycled, as raw material to produce the monomer ε-caprolactam.

In addition, since the partial degradation of the recovered PA6 is advantageous for the subsequent completion of depolymerization to ε-caprolactam, the stages of PA6 dissolution, separation of the fibrous material and coagulation of the solubilized PA6 can also be carried out in the presence of oxygen, in particular air, which, as is well known at high temperature leads to oxidation (and therefore chemical alteration) of PA6, thus simplifying the plant management of the process, as it is not necessary to adopt absolute inert atmosphere conditions (where the oxygen concentration is limited, under the worst conditions, to a few ppm), but only to guarantee the necessary blanketing conditions to avoid flammable or explosive conditions of the solvent.

A further advantage of the present invention lies in the fact that the recovered fibrous reinforcing material is of high quality, being substantially free from polymeric residues, and is therefore in a form suitable for reuse in the same or another production process, thus saving raw materials and energy, particularly in the case of glass or carbon fibres whose production processes are highly wasteful.

Thus, according to a first aspect, the present invention relates to a process for producing ε-caprolactam by depolymerizing polycaprolactam (PA6), comprising:

a. contacting a composite material comprising PA6 and at least one fibrous reinforcing material with a solvent comprising at least one polyol, at a temperature in the range 130° C.-200° C., so as to obtain a solution comprising solubilized PA6 and an insoluble fraction comprising at least said fibrous reinforcing material;
b. separating said insoluble fraction from said solution;
c. combining said solution with a coagulation liquid comprising water to obtain a partially depolymerized coagulated PA6 dispersed in a liquid phase;
d. separating said coagulated PA6 from said liquid phase;
e. subjecting said coagulated PA6 separated in said phase d to further depolymerization by hydrolysis to obtain ε-caprolactam.

The composite material usable for the purposes of the present invention comprises PA6 and at least one fibrous reinforcing material.

The fibrous reinforcing material comprises inorganic or organic fibres that are insoluble in the polyol used in the dissolution phase a, such as glass fibre, carbon fibre, polymeric fibre of polymers other than PA6 and mixtures of the aforementioned fibres. In one embodiment, the fibrous reinforcing material comprises at least glass fibres.

The composite material may also include one or more additional materials other than PA6 and reinforcing fibres. Examples of additional materials that may be present in the composite material include: dyes, UV absorbers, fillers, additives of various types (e.g. flame retardants, antistatic, antibacterial, nucleating agents, etc.) and other contaminants resulting from the use of the product or its recovery (e.g. additives that accumulate in the material as a result of previous mechanical recycling cycles).

Preferably, PA6 is present in the composite material in an amount in the range of 50%-95% by weight of the total weight of PA6 and the fibrous reinforcing material, more preferably in the range of 55%-90% by weight, even more preferably in the range of 60%-85% by weight.

Preferably, the fibrous reinforcing material is present in the composite material in an amount in the range of 5%-50% by weight of the total weight of the PA6 and the fibrous reinforcing material, more preferably in the range of 10%-45% by weight, even more preferably in the range of 15%-40% by weight.

In general, the composite material includes additional materials in an amount of up to 15% by weight of the total weight of the PA6 and the fibrous reinforcing material, preferably in an amount of up to 10% by weight, e.g. in the range of 1% to 5%.

Preferably, composite material includes post-consumer waste (end-of-life products) and/or post-industrial waste (waste from composite production processes).

The composite material can be fed to the process according to the present invention in different shapes and sizes. Preferably, the composite material is fed in fragments of approximately 1 to 3 mm in size, which can be obtained, for example, by pre-treatment by shredding or grinding the composite material.

The solvent used to dissolve the PA6 contained in the composite material comprises at least one polyol. Examples of polyols that may be used for the purposes of the present invention are ethylene glycol, diethylene glycol, triethylene glycol, propylene glycol, butylene glycol and glycerine. Polyols can be used singly or as a mixture of two or more polyols.

In a preferred embodiment, the solvent comprises or consists of at least one glycol, preferably chosen from: ethylene glycol, propylene glycol and mixtures thereof. In a particularly preferred form, the solvent is ethylene glycol.

Preferably, at stage a the weight ratio of composite material to solvent is in the range of 1:1 to 1:50, preferably in the range of 1:2 to 1:25.

In stage a, the composite material is placed in contact with the solvent to solubilize PA6 at a temperature in the range 130° C.-230° C., preferably in the range 150° C.-180° C.

Step a can be conducted, e.g. in a reactor, by keeping the mixture of solvent and composite material under agitation until the PA6 is completely dissolved.

Generally, the dissolution step lasts in the range of 0.5-6 hours, more preferably in the range of 2-4 hours.

Following the dissolution of the PA6, a biphasic mixture is present in the reactor consisting of a solution comprising the solubilized PA6 (liquid phase) and an insoluble fraction (solid phase) comprising the fibrous reinforcing material and any other materials or substances (e.g. small amounts of polymer additives) that are insoluble in the solvent at the operating conditions of stage a.

The insoluble fraction is then separated from the PA6 solution (stage b), e.g. by filtration or decantation. Advantageously, the separation is carried out hot, e.g. at a temperature in the range 130° C.-200° C., more preferably at the same temperature at which the polymer dissolution in stage a was carried out.

The viscosity of the solution containing the solubilized PA6 varies as a function of temperature and PA6 concentration. Generally, the PA6 solution presents itself as a clear, slightly viscous solution at the temperature at which stage a is carried out. If left to cool to room temperature, it forms a highly viscous, pasty mass without any solid-liquid phase separation.

The fibrous reinforcing material separated from the PA6 solution can advantageously be washed, for example, with the same solvent used for solubilization, to remove any residual polymer associated with it.

In the coagulation stage c, the PA6 solution is combined with a coagulation fluid including water to obtain a coagulated and partially depolymerized PA6. For that purpose, for example, the PA6 solution can be poured into a container containing the coagulation fluid. Preferably, the coagulation liquid is maintained at a temperature in the range 50° C.-95° C., more preferably in the range 80° C.-95° C.

Preferably, in the coagulation stage c, the weight ratio between the solution comprising the solubilized PA6 and the coagulation fluid is in the range of 1:1 to 1:10, preferably in the range of 1:1 to 1:5.

Preferably, the mixture of the PA6 solution with the coagulation liquid is cooled to room temperature with simultaneous gradual formation of the coagulated PA6 polymer, which remains dispersed in the liquid phase comprising the solubilization solvent and water. The coagulated polymer may appear, for example, in the form of irregularly shaped particles approximately 1-5 mm in size.

In stage d, the coagulated PA6 is separated from the liquid phase "solvent/coagulation liquid", e.g. by filtration. Preferably, the coagulated PA6 is washed with water to remove the residual solvent present.

Advantageously, in one embodiment, the water stream used for washing the coagulated PA6 and also containing a proportion of solvent is collected together with the stream of the liquid phase solvent/coagulation liquid generated by the separation of the coagulated PA6.

In one embodiment, at least part of the mixture of the above two streams is recycled directly to the step c, where it is used as coagulation liquid.

In a further embodiment, at least part or the entire mixture of these two streams undergoes a treatment to separate the solvent from the coagulation liquid (e.g. water).

For example, the mixture of the above two streams, containing the solvent and the coagulation liquid, e.g. glycol and water, undergoes a separation process by distillation. The evaporated phase, comprising the coagulation liquid (water) and modest amounts of solvent, can be reused in the coagulation step c, while the bottom liquid phase of the distillation, essentially comprising the solvent, can be reused in stage a for the treatment of further composite material.

The extent of partial depolymerization of coagulated PA 6 can be assessed by determining the relative viscosity value (Relative Viscosity—ISO 307 or ASTM 789).

The amount of carboxyl groups that are esterified as a result of the solubilization and coagulation treatment of PA6 can be determined by NMR analysis as described in the examples.

By the process according to the present invention, it is possible to obtain a coagulated and partially depolymerized PA6 at the end of stage d which has an amount of terminal carboxylic groups esterified with solvent molecules, in particular ethylene glycol, preferably less than 2.0% by weight with respect to the weight of the dry coagulated PA6.

The coagulated and partially depolymerized PA6 obtained as described above can be fed to the next hydrolytic depolymerization stage (stage e) to complete depolymerization and obtain the monomer ε-caprolactam.

The hydrolytic depolymerization stage can be conducted in accordance with processes known to a person skilled in the art.

In general, coagulated and partially depolymerized PA6 can be reacted with water in the form of a vapour stream, preferably in the presence of an acid catalyst.

PA6 preferably undergoes hydrolytic depolymerization, using a superheated vapour stream, at a temperature in the range 200° C.-450° C., e.g. at a pressure of 0.2-20 bar.

For this purpose, the PA6 is fed, preferably in a molten state, e.g. via extruder/pre-melter, to a depolymerization reactor. However, the PA6 can also be fed to the reactor in solid granule form, e.g. via a hopper and/or dosing auger.

The vapour, which is superheated to prevent its re-condensation inside the reactor, is preferably distributed in the melt in order to maintain a continuous homogeneous distribution and promote capillary contact with the melt while at the same time ensuring its continuous agitation and homogenization.

The acid catalyst can be one of those known to a person skilled in the art, chosen for example from inorganic acids (e.g. orthophosphoric acid and boric acid), organic acids (e.g. p-toluenesulphonic acid) and ammonium phosphate salts.

The monomer ε-caprolactam that is formed during depolymerization is separated in the gas phase from the depolymerization mixture, e.g. by a stream of water vapour, and then condensed.

For example, the vapours leaving the reactor can be conveyed to a condensation system by direct contact with water, which makes it possible to separate two streams: a first stream essentially consisting of vapour only; a second stream consisting of an aqueous solution containing crude ε-caprolactam (being already a high purity one, however) at a concentration of 50% or more.

The condensed monomer is then subjected to purification using methods known to a person skilled in the art, e.g. by solvent or solvent-free extraction (as described in e.g. US 20190382339), hydrogenation, treatment with potassium permanganate and distillation to separate light and heavy by-products.

An example of a possible embodiment of the process according to the present invention is described below with reference to the following figure:

FIG. 1, schematic representation of the process to produce ε-caprolactam according to the present invention wherein: "PA6 with GF" means a composite material comprising polyamide and glass fibre as reinforcing material; "EG" is ethylene glycol.

In FIG. 1, the composite material 1 is fed to a crushing step 2 to obtain fragments of small size, e.g. 1-3 mm. The crushed composite material 3 is then subjected to a dissolution step 4 in EG solvent at a temperature of 130-200° C. in which a biphasic mixture 5 comprising PA6 solubilized in EG and an insoluble fraction in suspension comprising glass fibres is generated. The solvent EG used for dissolution (stream 37) is taken from a storage unit 28.

In a subsequent filtration step 6, the insoluble fraction 7 comprising the glass fibres is separated from the solubilized PA6 8, e.g. by hot filtration at the same temperature as the dissolution step 4. The glass fibre of the insoluble fraction 7 is then subjected to a washing step 9, using a stream of recycled glycol 10 from the storage unit 11, and then extracted from the process (stream 12). The glycol used for washing is recycled (stream 13) partly to the coagulation unit 15 (stream 13*a*) and partly to the storage unit 11 (stream 13*b*) to which a make-up glycol stream 14 is also fed.

The solubilized PA6 stream 8 is subjected to a coagulation step 15 by placing it in contact with a water stream 17. The coagulation produces PA6 granules in a partially depolymerized form dispersed in a liquid phase of water and EG (stream 16) that is fed to a subsequent filtration step 21. The water stream 17 used for coagulation comes from a water storage 18 unit, which is also fed a water stream 19 from the condensation phase 33 following the distillation phase 30 of the water/EG mixture and a make-up water stream 20.

In the filtration step 21, the stream 16 of PA6 granule dispersion is separated into a stream 22 of coagulated PA6 granules and a stream 23 comprising a water/EG mixture. The coagulated PA6 granules 22 are then subjected to a washing and drying step 24 to obtain dried granules 25. A water stream 26*a* is used for washing, which is then partially recycled (stream 35) to the storage unit 27, to which the water/EG mixture 23 from the filtration step 21 is also fed.

The stream 29 of the water/EG mixture contained in the storage unit 27 is subjected to a distillation step 30 from which a stream 31 of EG and a vapour stream 32 are obtained which, after being subjected to the condensation step 33, generates a stream 34 of water containing traces of EG separated from the cycle and a main stream 19, which is sent to the storage unit 18 for its reuse in the coagulation step 15.

The stream 31 of EG recovered from distillation is collected in the storage unit 28, to which a current of make-up EG 36 is also fed.

The following examples are provided purely for the purpose of illustration of the present invention and should not be regarded as a limitation of the scope of protection defined by the appended claims.

In the examples, the relative viscosity (RV) was measured according to the ISO 307 method (1% in $H_2SO_4$).

EXAMPLES

Reference Example (Comparative): Direct Hydrolytic Depolymerization of a Composite Material (PA6 GF30)

In a pilot reactor, equipped with a heating jacket and with a volume of approximately 100 litres, 30 kg of granules of a commercial composite material called "PA6 GF30" containing 70% by weight PA6 and 30% by weight glass fibre were loaded, for a total of 21 kg PA6 and 9 kg glass fibre (relative viscosity (RV) of PA6: 2.7; fibre diameter: 11 μm; fibre length: 4.5 mm; glass: E-Glass(DIN 1259)).

The composite material underwent hydrolytic depolymerization in the presence of an acid catalyst to obtain caprolactam monomer, operating at atmospheric pressure and a temperature in the range of 250-300° C.

As depolymerization continued, which could not in fact be carried out for more than 20-30% of the loaded material, the progressive accumulation of glass fibres inside the reactor was observed, which led to the inability to discharge the residual depolymerization mixture through the bottom valve. In order to restore the plant, it was necessary to dismantle the reactor and break up the solid mass formed by mechanical means, replacing some of the clogged parts.

This test shows that it is not possible to depolymerize a composite material containing an inorganic fibrous reinforcing material.

Example 1: Testing the Solubility of PA6 in Ethylene Glycol 1000 g of ethylene glycol (EG) and 50 g of PA6 granules (PA6:EG ratio of 1:20) were loaded into an apparatus equipped with a reflux condenser, temperature control thermometer and heating system. The PA6 had a relative viscosity RV=2.7, corresponding to polymer chains with an average molecular weight of 19500. The mixture was gradually heated under continuous stirring to approximately 135° C., where complete dissolution of the polymer was observed with the formation of a transparent yellow solution. The PA6 solution was heated up to 150° C. and kept at this temperature for about 1 h without observing the formation of any precipitate. The mixture was then allowed to cool to room temperature, becoming a consistent, non-filterable paste-like mass (no solid/liquid phase separation).

Examples 2 and 3: Testing the Maximum Solubilization of PA6 in Ethylene Glycol (EG) at Temperatures Below the Boiling Point of the EG Ethylene glycol has a boiling point of 195° C. In order to operate equipment at atmospheric pressure, the concentrations at which complete dissolution of the polymer can be achieved below 195° C. were tested. For this purpose, following the same process as in Example 1, dissolution tests were carried out using the quantities of PA6 and EG shown in Table 1. Table 1 also shows the temperatures at which complete dissolution of PA6 was observed (Dissol. Temp.) and the maximum temperature (Max. Temp.) at which the solution was maintained (1 h) after the complete dissolution of the PA6.

TABLE 1

| Example No. | PA6 (RV 2.7) g | EG g | Ratio EG/PA6 | Dissol. temp. ° C. | Max. temp. ° C. | Precipitation |
|---|---|---|---|---|---|---|
| 1 | 50 | 1000 | 20 | 135 | 170-180 | No precipitate |
| 2 | 200 | 1000 | 5 | 160 | 170-180 | No precipitate |
| 3 | 250 | 1000 | 4 | 170 | 180 | No precipitate |

Based on the data obtained in Examples 1 to 3, the dissolution of the PA6 in ethylene glycol, below the boiling point of the solvent (195° C.) and atmospheric pressure, shows a substantially linear trend.

The PA6 solutions of Examples 2 and 3 also form a consistent, non-filterable pasty mass after cooling to room temperature.

Example 4: Dissolution of a PA6 GF30 Composite Material With a High Solvent/Polymer Ratio The dissolution test of Example 1 on the composite material PA6 GF30 was repeated under the conditions shown in Table 2.

TABLE 2

| Example No. | PA6 30 GF g | PA6 g | GF g | EG g | EG/PA6 30GF ratio | EG/PA6 ratio | Dissol. Temp. ° C. | T max ° C. | Time at T max minutes |
|---|---|---|---|---|---|---|---|---|---|
| 4 | 50 | 35 | 15 | 1000 | 20 | 28.5 | 150 | 170-180 | 120 |

At the end of the test, a suspension of a white solid in a yellowish solution was obtained. The suspension was filtered in a filter maintained at 170° C., and then the operations described below were performed:

The white solid remaining in the filter was washed with 50 g of hot ethylene glycol (temp. 150-170° C.) and then with small amounts of $H_2O$ to obtain a fluffy-looking solid, which was then dried at 70° C.

The clear solution obtained by filtration at 170° C. (filtrate), amounting to 1035 g, mixed with the 50 g of water used to wash the solid (for a total of 1085 g), was poured into 4000 g of $H_2O$ at 90° C. under agitation, resulting in a mixture with coagulated PA6 suspended in the liquid phase.

The weight ratio of $H_2O$ to PA6 solution in EG was 4000:1085=3.7; the $H_2O$:PA6 ratio was 4000:35=114; the $H_2O$:EG ratio was 4000:1050=3.8.

The mixture containing the coagulated PA6 was filtered at room temperature to obtain a yellowish solid, which was then washed with a little water to remove any glycol remaining on the surface. After drying, the solid was subjected to the analytical determinations in Table 3.

TABLE 3

| Example 4 | | |
|---|---|---|
| Taste-olfactory | Results | Notes |
| FTIR | Polymer PA6 | |
| Ashes | Absent | |
| Viscosity RV at 1% in $H_2SO_4$ | 1.8 | RV of PA6 of composite PA6 GF30 = 2.7 |
| Amine groups NH2, meq/kg | 13.8 | Initial NH2 = 35 meq/kg |
| COOH carboxyl groups, meq/kg | 34.6 | Initial COOH = 50 meq/kg |

The amounts of amine and carboxyl groups in the polymer were determined by potentiometric titration.

The data in Table 3 show that the PA6 polymer, which was completely separated from the glass fibre, underwent partial depolymerization of the polymer chains (the RV value dropped from 2.7 to 1.8). Partial depolymerization promotes the subsequent chemical recovery of the ε-caprolactam monomer. In fact, the average chain length of the polymer having RV 2.7 corresponds to approximately 19500/113=170 units, whereas that of the coagulated polymer having RV 1.8 corresponds to approximately 9200/113=80 (the relationship between the average molecular weight and the RV index is Mw=11500 (RV-1); the molecular weight of the repeating unit of PA6 is 113).

Examples 5 and 6: Dissolution of PA6 GF30 at Reduced Solvent/Polymer Ratio

The process in Example 4 was repeated by increasing the amount of composite material treated, with the same volumes of EG and coagulation water.

The composition of the mixture and the dissolution conditions adopted in the tests are shown in Table 4.

Examples 5 and 6 differ in terms of the time for which the PA6 solution was kept the maximum dissolution temperature (2 hours for example 5; 4 hours for example 6), in order to verify the possible influence of this operating condition on the extent of esterification of the PA6 end groups with EG, all other conditions being equal.

TABLE 4

| Example No. | PA6 30 GF g | PA6 g | GF g | EG g | EG/PA6 30GF ratio | EG/PA6 ratio | Dissol. Temp. ° C. | T max ° C. | Time at T max minutes |
|---|---|---|---|---|---|---|---|---|---|
| 5 | 250 | 175 | 75 | 1000 | 4 | 5.7 | 170 | 170-180 | 120 |
| 6 | 250 | 175 | 75 | 1000 | 4 | 5.7 | 170 | 170-180 | 240 |

At the end of the test, a suspension of a white solid in a yellowish solution was obtained. The suspension was filtered in a filter maintained at 180° C., and then the operations described below were performed:

The white solid remaining in the filter was washed with 50 g of hot ethylene glycol and then with small amounts of $H_2O$, obtaining a fluffy-looking solid that was then dried at 70° C.;

The clear solution obtained by filtration at 180° C. (filtrate), amounting to 1175 g, mixed with the 50 g of water used to wash the solid (for a total of 1225 g), was poured into 4000 g of $H_2O$ at 90° C. under agitation, resulting in a mixture with coagulated PA6 suspended in the liquid phase.

The weight ratio of $H_2O$ to PA6 solution in EG was 4000:1225=3.3; the $H_2O$:PA6 ratio was 4000:155=22.8; the $H_2O$:EG ratio was 4000:1050=3.8.

The mixture containing the coagulated PA6 was filtered at room temperature to obtain a yellowish solid, which was then washed with a little water to completely remove any glycol remaining on the surface. After drying, the solid was subjected to the analytical determinations in Table 4.1 for Example 5 and 4.2 for Example 6.

TABLE 4.1

| Example 5 | | |
|---|---|---|
| Taste-olfactory | Results | Notes |
| FTIR | Polymer PA6 | |
| Ashes | Absent | |
| Viscosity RV at 1% in | 1.58 | RV of PA6 of composite |

TABLE 4.1-continued

| Example 5 | | |
|---|---|---|
| Taste-olfactory | Results | Notes |
| $H_2SO_4$ | | PA6 GF30 = 2.7 |
| Amine groups NH2, meq/kg | 57.5 | Initial NH2 = 35 meq/kg |
| COOH carboxyl groups, meq/kg | 47.6 | Initial COOH = 50 meq/kg |

Even at significantly higher concentrations of PA6 30GF composite material in EG than in Example 4, it is possible to separate the PA6 polymer from the composite material and recover PA6 in a partially depolymerized form (RV=1.58). The average chain length of the polymer changes from a value of 19500/113=170 units of the initial polymer having RV=2.7 to approximately 6670/113=60 of the recovered polymer having RV=1.58.

TABLE 4.2

| Example 6 | | |
|---|---|---|
| Taste-olfactory | Results | Notes |
| FTIR | Polymer PA6 | |
| Ashes | Absent | |
| Viscosity RV at 1% in $H_2SO_4$ | 1.62 | RV of PA6 of composite PA6 GF30 = 2.7 |
| Amine groups NH2, meq/kg | 73.15 | Initial NH2 = 35 meq/kg |
| COOH carboxyl groups, meq/kg | 52.7 | Initial COOH = 50 meq/kg |

Also in Example 6, again with significantly higher concentrations of PA6 30GF composite material in EG than in Example 4, it is possible to separate the PA6 polymer from the composite material and recover PA6 in a partially depolymerized form (RV=1.62). Extending the time to the maximum dissolution temperature does not cause esterification of the end groups. In this case, the average chain length of the polymer changes from a value of 19500/113=170 units of the initial polymer having RV=2.7 to approximately 7130/113=63 units of the recovered polymer having RV=1.62.

Example 7: Dissolution of "PA6 GF20" (PA6 Loaded With Different 20% Glass Fibre by Weight)

The process of examples 5 and 6 was repeated using the composite material "PA6 GF20" (80% by weight PA6, 20% by weight glass fibre).

The composition of the mixture and the dissolution conditions adopted in the test are shown in Table 5.

TABLE 5

| Example No. | PA6 20 GF g | PA6 g | GF g | EG g | EG/PA6 20 GF ratio | EG/PA6 ratio | Dissol. Temp. ° C. | T max ° C. | Time at T max minutes |
|---|---|---|---|---|---|---|---|---|---|
| 7 | 250 | 200 | 50 | 1000 | 4 | 5 | 170 | 170-180 | 120 |

At the end of the test, a suspension of a white solid in a yellowish solution was obtained. The suspension was filtered and the separated coagulated solid was washed as described in Example 5. After drying, the solid was subjected to the analytical determinations in Table 6.

This example shows that even with different concentrations of the glass fibre, it is possible to separate the PA6 polymer from the composite material and recover the PA6 in a partially depolymerized form (RV=1.61). The average chain length of the polymer changes from a value of 19500/113=170 units of the initial polymer having RV=2.7 to approximately 7015/113=62 units of the recovered polymer having RV=1.61.

TABLE 6

| Example 7 | | |
|---|---|---|
| Taste-olfactory | Results | Notes |
| FTIR | Polymer PA6 | |
| Ashes | Absent | |
| Viscosity RV at 1% in $H_2SO_4$ | 1.61 | RV of PA6 of composite PA6 GF20 = 2.7 |
| Amine groups NH2, meq/kg | 76.7 | Initial NH2 = 35 meq/kg |
| COOH carboxyl groups, meq/kg | 53.2 | Initial COOH = 50 meq/kg |

Example 8: Dissolution of PA6 GF30 With Reduction of Solvent/Polymer Ratio

The process of Examples 5 and 6 was repeated using the composite material "PA6 GF30" (30% by weight glass fibre).

The composition of the mixture and the dissolution conditions adopted in the tests are shown in Table 7. In particular, in this example, the amount of glycol used was reduced in relation to the PA6 GF30 composite.

TABLE 7

| Example No. | PA6 30 GF g | PA6 g | GF g | EG g | EG/PA6 30GF ratio | EG/PA6 ratio | Dissol. Temp. ° C. | T max ° C. | Time at T max minutes |
|---|---|---|---|---|---|---|---|---|---|
| 8 | 250 | 175 | 75 | 750 | 3 | 4.3 | 170 | 170-180 | 80 |

After dissolution, the resulting solution was subjected to the coagulation, filtration and washing process described in Example 5. After drying, the solid was subjected to the analytical determinations in Table 8.

This example shows that even with a smaller amount of glycol it is possible to separate the PA6 polymer from the composite material and recover PA6 in a partially depolymerized form (RV=1.95).

The average chain length of the polymer changes from a value of 19500/113=170 units of the initial polymer having RV=2.7 to approximately 10925/113=97 units of the recovered polymer having RV=1.95.

TABLE 8

| Example 8 | | |
|---|---|---|
| Taste-olfactory | Results | Notes |
| FTIR | Polymer PA6 | |
| Ashes | Absent | |
| Viscosity RV at 1% in $H_2SO_4$ | 1.95 | RV of PA6 of composite PA6 GF30 = 2.7 |
| Amine groups NH2, meq/kg | 43.8 | Initial NH2 = 35 meq/kg |
| COOH carboxyl groups, meq/kg | 29.1 | Initial COOH = 50 meq/kg |

Example 9: Suitability of PA6 Separated From the Composite Material for Depolymerization to ε-Caprolactam The suitability of the PA6 recovered from the composite material for depolymerization to the monomer ε-caprolactam was studied by NMR spectroscopy. For the purposes of the present invention, a PA6 is considered suitable for hydrolytic depolymerization when the conditions in Table 9 are met.

TABLE 9

| Parameter | Maximum acceptable limit for the depolymerization process |
|---|---|
| PA6 content | >=90% |
| Inorganic substances | 3% max |
| Other polymers | 6% max |
| Other non-hazardous substances* | 1% max |
| Halogenated compounds | <50 ppm |

*Additives present in the recovered polymer (e.g. thermal stabilizing agents, antioxidants, dyes, etc.)

Feeding to hydrolytic depolymerization of a PA6 that does not meet one or more of the requirements in Table 9 may affect the activity of the catalyst or the quality of the ε-caprolactam obtained (e.g. presence of undesirable by-products, development of corrosive inorganic acids, etc.)

The coagulated PA6 granules of examples 4 (RV=1.8), 5 (RV=1.58) and 6 (RV 1.62), after separation, washing and drying, were analysed by 1D and 2D NMR spectroscopy (1H and 13C). To this end, 51 mg of PA6 from example 4, 54 mg of PA6 from example 5 and 52 mg from example 6 were each solubilized in 600 mL of deuterated trifluoroethanol ($CF_3CD_2OD$) after heating for a few minutes. From the NMR spectra of the three samples thus prepared, the parameters shown in Table 10 were determined.

TABLE 10

| | Ethylene glycol | PA6 | PA6 with glycol-esterified ends | Total |
|---|---|---|---|---|
| Example 4 | 0.6% | >98.9% | <0.5% | 100% |
| Example 5 | 0.3% | 98.3% | 1.4% | 100% |
| Example 6 | 0.1% | 97.9 | 2.0% | 100% |

The data in Table 10 confirm the suitability of the PA6 recovered from the composite material to undergo hydrolytic depolymerization; it can be seen that the useful PA6 content is well above the specification limit set at 90%.

Example 10: Depolymerization of PA6 Separated From the Composite Material

With the aim of recovering the PA6 polymer separated from the glass fibre for the purposes of a depolymerization test, the process described in Example 4 was repeated on a sample of PA6 30GF composite material, using a 50-litre reactor equipped with a reflux condenser, thermometer for temperature control and an oil-bath heating system. In the reactor, 20 kg of ethylene glycol (EG) and 5 kg of PA6 30FV granules were loaded, for a total of 25 kg.

The mixture was gradually heated under continuous stirring to approximately 170-180° C., where complete dissolution of the polymer was observed, and then kept at this temperature for approximately 2 h. From the bottom valve, the suspension, which was kept warm at all times, was directly percolated over a pilot filter (Nutsche type) under a slight vacuum and then allowed to flow into a 120-litre mobile reactor, equipped with an air agitator, in which 80 litres of demineralized water at room temperature were present as coagulation liquid. The PA6 was drained from the reactor in such a way as to leave the glass fibre inside the filter system wet on the surface by a light layer of PA6 solution in glycol.

The coagulated solid in the form of irregular, yellowish-looking granules was filtered, washed through the filter with water and, once discharged, dried in an oven at 70° C. under a slight vacuum to a moisture content of less than 0.5% by weight.

Approximately 3.0 kg of PA6 with an RV of 1.6 was obtained, as also observed in the tests in Examples 4, 5 and 6. In particular, in the dried PA6, ash was essentially absent, thus confirming the absence of residual glass fibre.

The glass fibre separation pre-treatment described above was repeated on four aliquots of PA6 GF30 until a quantity of 12.34 kg of dried PA6 was collected.

The PA6 polymer thus recovered, free of glass fibre, was loaded into a pilot reactor (volume approximately 50 litres) made of an acid-resistant alloy similar to that of the Reference Example, equipped with a heating jacket and superheated steam supply system.

The material underwent hydrolytic depolymerization in the presence of an acid catalyst to obtain caprolactam monomer, operating at atmospheric pressure and a temperature in the range of 250-300° C.

The PA6 polymer was fed to the reactor directly in its solid granule form via a hopper and/or dosing auger system. The acid catalyst and vapour superheated above 300° C. were then also fed into the reactor. The vapours leaving the reactor were fed to a condensation system by direct contact with water, separating a first fraction containing only vapour and a second fraction comprising an aqueous solution of crude ε-caprolactam (concentration approx. 50% by weight). The crude ε-caprolactam solution was then put through a conventional purification process, resulting in a final product in line with commercial specifications (in terms of acidity, alkalinity, volatile bases, APHA, optical density and permanganate index).

During depolymerization, no clogging phenomenon as described in the comparative example was observed, and the speed of the depolymerization process was higher than that observed for the depolymerization of PA6 waste materials in which the polymer had retained the RV of 2.7 as, for example, that recovered from carpet separation.

Table 11 below shows the data of the depolymerization performed on the coagulated PA6 of example 10 in comparison with a reference material consisting of post-consumer carpet waste having the following composition: 90% by weight of PA6 (RV=2.7), 10% by weight of other materials (mainly polypropylene, polyethylene terephthalate, adhesives and additives).

TABLE 11

| | | PA6 from carpet waste (90% by weight of PA6, RV 2.7) | PA6 coagulated Ex. 10 (98% by weight of PA6, RV 1.6 |
|---|---|---|---|
| Quantity loaded | Kg | 12 (equivalent to 10.8 kg PA6) | 12.34, (equivalent to 12.2 kg PA6) |
| Crude caprolactam solution | Kg | 18.5 | 20.8 |
| Concentration of PA6 in crude caprolactam solution | % | 50.2% | 55.3% |
| Total crude caprolactam | Kg | 9.3 | 11.5 |
| Caprolactam recovery yield from depolymerization | | 86.1% | 93.2% |
| Residual sludge | Kg | 3.3 | 1.6 |

The coagulated PA6 obtained after glass fibre separation proved to be perfectly depolymerizable, like the best PA6 rejects recovered from the separation of polyamide from carpets, but with higher yields and concentrations of the final solution under the same experimental test conditions.

The invention claimed is:

1. A process for producing ε-caprolactam by depolymerization of polycaprolactam (PA6), comprising:

contacting a composite material comprising PA6 and at least one fibrous reinforcing material with a solvent comprising at least one polyol, at a temperature of 130° C. to 200° C., to obtain a solution comprising solubilized PA6 and an insoluble fraction comprising the at least one fibrous reinforcing material;

separating the insoluble fraction from the solution;

combining the solution with a coagulation liquid comprising water to obtain a partially depolymerized coagulated PA6 dispersed in a liquid phase;

separating the coagulated PA6 from the liquid phase; and subjecting the coagulated PA6 separated from the liquid phase to further depolymerization by hydrolysis to obtain ε-caprolactam.

2. The process according to claim 1, wherein, when combining the solution with the coagulation liquid, the coagulation liquid has a temperature of 50° C. to 95° C.

3. The process according to claim 1, wherein the composite material comprises PA6 in an amount of 50% to 95% by weight with respect to a total weight of PA6 and the fibrous reinforcing material.

4. The process according to claim 1, wherein the composite material comprises the fibrous reinforcing material in an amount of 5% to 50% by weight with respect to a total weight of PA6 and the fibrous reinforcing material.

5. The process according to claim 1, wherein the solvent comprises at least one glycol.

6. The process according to claim 5, wherein the solvent comprises at least one selected from the group consisting of ethylene glycol, diethylene glycol, triethylene glycol, propylene glycol, and butylene glycol.

7. The process according to claim 1, wherein contacting the composite material with the solvent comprises contacting at a temperature of 150 to 170° C.

8. The process according to claim 1, wherein contacting the composite material with the solvent comprises contacting at a weight ratio of the composite material to the solvent of 1:1 to 1:50.

9. The process according to claim 1, wherein combining the solution with the coagulation liquid comprises combining at a weight ratio of the solution to the coagulation liquid of 1:1 to 1:10.

10. The process according to claim 1, wherein the depolymerization by hydrolysis is carried out in the presence of at least one acid catalyst.

11. The process according to claim 1, wherein, when combining the solution with the coagulation liquid, the coagulation liquid has a temperature of 80° C. to 95° C.

12. The process according to claim 1, wherein the composite material comprises PA6 in an amount of 55% to 90% by weight with respect to a total weight of PA6 and the fibrous reinforcing material.

13. The process according to claim 1, wherein the composite material comprises PA6 in an amount of 60% to 85% by weight with respect to a total weight of PA6 and the fibrous reinforcing material.

14. The process according to claim 1, wherein the composite material comprises the fibrous reinforcing material in an amount of 10% to 45% by weight with respect to a total weight of PA6 and the fibrous reinforcing material.

15. The process according to claim 1, wherein the composite material comprises the fibrous reinforcing material in an amount of 15% to 40% by weight with respect to a total weight of PA6 and the fibrous reinforcing material.

16. The process according to claim 1, wherein contacting the composite material with the solvent comprises contacting at a weight ratio of the composite material to the solvent of 1:2 to 1:25.

17. The process according to claim 1, wherein combining the solution with the coagulation liquid comprises combining at a weight ratio of the solution to the coagulation liquid of 1:1 to 1.

* * * * *